United States Patent [19]

Daum et al.

[11] Patent Number: 4,752,607
[45] Date of Patent: Jun. 21, 1988

[54] ALKOXYCARBONYL-SUBSTITUTED HYDROXYTHIOPHENE-CARBOXAMIDES, FUNGICIDAL COMPOSITIONS AND USE

[75] Inventors: Werner Daum, Krefeld; Gerd Hänssler, Leverkusen, both of Fed. Rep. of Germany

[73] Assignee: Bayer Aktiengesellschaft, Leverkusen, Fed. Rep. of Germany

[21] Appl. No.: 875,427

[22] Filed: Jun. 17, 1986

[30] Foreign Application Priority Data

Jun. 29, 1985 [DE] Fed. Rep. of Germany ....... 3523313
Jan. 31, 1986 [DE] Fed. Rep. of Germany ....... 3602889

[51] Int. Cl.⁴ .................. A01N 43/10; A01N 43/84; C07D 333/38; C07D 413/06
[52] U.S. Cl. .................. 514/212; 514/252; 514/326; 514/365; 514/374; 514/422; 514/445; 514/231.5; 540/596; 544/58.7; 544/146; 544/379; 546/212; 546/213; 548/200; 548/215; 549/64
[58] Field of Search ............... 540/596; 544/58.7, 146, 544/379; 546/212, 213; 548/200, 215; 549/64; 514/212, 222, 230, 252, 326, 365, 374, 422, 445

[56] References Cited

U.S. PATENT DOCUMENTS 2,453,102 11/1948 Turnbull ................... 549/64

FOREIGN PATENT DOCUMENTS 32784  7/1981 European Pat. Off. .
0093384 11/1983 European Pat. Off. .
1020641 12/1957 Fed. Rep. of Germany .

OTHER PUBLICATIONS

10th Intern. Congress of Plant Protection, Nov. 20–25, 1983, Brighton, vol. 1, 400–407.

Primary Examiner—Robert W. Ramsuer
Attorney, Agent, or Firm—Sprung, Horn, Kramer & Woods

[57] ABSTRACT

Alkoxycarbonyl-substituted hydroxythiophenecarboxamides of the formula

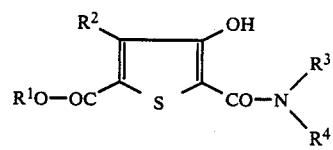

in which
$R^1$ represents alkyl, alkoxyalkyl, alkylthioalkyl, fluoroalkyl, cyanoalkyl, alkenyl or alkinyl or represents cycloalkyl,
$R^2$ represents alkyl or optionally substituted phenyl,
$R^3$ represents alkyl, alkoxyalkyl, alkylthioalkyl, cyanoalkyl, fluoroalkyl, alkenyl, alkinyl, cycloalkyl or alkoxy and
$R^4$ represents hydrogen, alkyl, alkoxyalkyl, alkylthioalkyl, fluoroalkyl, cyanoalkyl, alkenyl, alkinyl or cycloalkyl, or
$R^3$ and $R^4$, together with the nitrogen atom, represent a heterocyclic radical which is optionally substituted by alkyl and can be further substituted in the alkylene chain by oxygen, sulphur or nitrogen, are useful as fungicides and intermediates.

8 Claims, No Drawings

ALKOXYCARBONYL-SUBSTITUTED HYDROXYTHIOPHENE-CARBOXAMIDES, FUNGICIDAL COMPOSITIONS AND USE

The present invention relates to new alkoxycarbonyl-substituted hydroxythiophene-carboxamides, a process for their preparation and their use as fungicides and as intermediate products.

It is already known that 2,5-bis-(alkoxycarbonyl)-3,4-bis-(acyloxy)-thiophenes and 2,5-bis-(alkoxycarbonyl)-3-alkyl-4-acyloxythiophenes have fungicidal properties (compare European Pat. No. 32,784 and European Pat. No. 93,384). 2,5-Bis-(isopropoxycarbonyl)-3-methyl-4-(3-methylbenzoyloxy)-thiophene, which is known from T. Wada et al, Proceedings of the 10th Intern. Congress of Plant Protection, Nov. 20–25, 1983, Brighton, Volume 1, 400–407, may be mentioned here in particular.

New alkoxycarbonyl-substituted hydroxythiophene-carboxamides of the general formula (I)

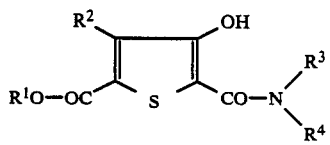

in which
$R^1$ represents alkyl, alkoxyalkyl, alkylthioalkyl, fluoroalkyl, cyanoalkyl, alkenyl or alkinyl or represents cycloalkyl,
$R^2$ represents alkyl or optionally substituted phenyl,
$R^3$ represents alkyl, alkoxyalkyl, alkylthioalkyl, cyanoalkyl, fluoroalkyl, alkenyl, alkinyl, cycloalkyl or alkoxy and
$R^4$ represents hydrogen, alkyl, alkoxyalkyl, alkylthioalkyl, fluoroalkyl, cyanoalkyl, alkenyl, alkinyl or cycloalkyl, or
$R^3$ and $R^4$, together with the nitrogen atom, represent a heterocyclic radical which is optionally substituted by alkyl and can be further substituted in the alkylene chain by oxygen, sulphur or nitrogen,
have been found.

It has furthermore been found that the new alkoxycarbonyl-substituted hydroxythiophene-carboxamides of the formula (I)

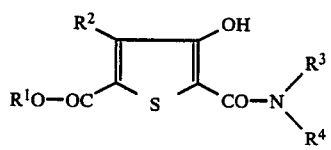

in which
$R^1$ represents alkyl, alkoxyalkyl, alkylthioalkyl, fluoroalkyl, cyanoalkyl, alkenyl or alkinyl or represents cycloalkyl,
$R^2$ represents alkyl or optionally substituted phenyl,
$R^3$ represents alkyl, alkoxyalkyl, alkylthioalkyl, cyanoalkyl, fluoroalkyl, alkenyl, alkinyl, cycloalkyl or alkoxy and
$R^4$ represents hydrogen, alkyl, alkoxyalkyl, alkylthioalkyl, fluoroalkyl, cyanoalkyl, alkenyl, alkinyl or cycloalkyl, or
$R^3$ and $R^4$, together with the nitrogen atom, represent a heterocyclic radical which is optionally substituted by alkyl and can be further substituted in the alkylene chain by oxygen, sulphur or nitrogen,
are obtained by a process in which a carboxylic acid derivative of the formula (II)

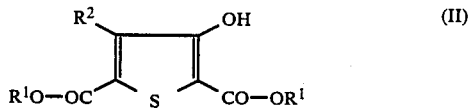

in which
$R^1$ and $R^2$ have the abovementioned meanings,
is reacted with an amine of the formula (III)

in which
$R^3$ and $R^4$ have the abovementioned meanings,
if appropriate in the presence of a solvent or diluent and if appropriate in the presence of a tertiary organic base.

It has furthermore been found that the new alkoxycarbonyl-substituted hydroxythiophene-carboxamides of the formula (I) have fungicidal properties and are also suitable as intermediate products for the synthesis of active compounds.

Surprisingly, the alkoxycarbonyl-substituted hydroxythiophene-carboxamides of the formula (I) according to the invention exhibit a better fungicidal activity than the 2,5-bis-(isopropoxycarbonyl)-3-methyl-4-(3-methylbenzoyloxy)-thiophene known from the prior art.

Formula (I) provides a general definition of the alkoxycarbonyl-substituted hydroxythiophene-carboxamides according to the invention. Preferred compounds of the formula I are those
in which
$R^1$ represents alkyl with 1 to 5 carbon atoms, or represents alkoxyalkyl or represents alkylthioalkyl with 1 to 5 carbon atoms per alkyl part, or represents fluoroalkyl with in each case up to 5 fluorine and carbon atoms, or represents cyanoalkyl with 1 to 5 carbon atoms in the alkyl part, or represents alkenyl with 3 or 4 carbon atoms, or represents alkinyl with 3 to 5 carbon atoms, or represents cycloalkyl with 4 to 6 carbon atoms,
$R^2$ represents alkyl with 1 to 4 carbon atoms or optionally mono- to independently penta-substituted phenyl, substituents being alkyl with 1 to 4 carbon atoms, alkoxy or alkylthio with 1 to 4 carbon atoms in each case, halogen, nitro, halogenalkyl, halogenoalkoxy or halogenoalkylthio with 1 to 4 carbon atoms and 1 to 5 halogen atoms in each case (halogen means fluoro, chloro, bromo and iodo, preferably fluoro and chloro),
$R^3$ represents alkyl with 1 to 5 carbon atoms, or represents alkoxyalkyl or alkylthioalkyl with in each case 1 to 5 carbon atoms per alkyl part, or represents cyanoalkyl with 1 to 5 carbon atoms in the alkyl part, or represents fluoroalkyl with up to 3 fluorine atoms and up to 5 carbon atoms, or represents alkenyl or alkinyl with 3 to 5 carbon atoms, or represents cycloalkyl with 3 to 6 carbon atoms, or represents alkoxy with 1 to 5 carbon atoms and
$R^4$ represents hydrogen or alkyl with 1 to 5 carbon atoms, or represents alkoxyalkyl or alkylthioalkyl with in each case 1 to 5 carbon atoms per alkyl part, or represents cyanoalkyl with 1 to 5 carbon atoms in the alkyl part, or represents fluoroalkyl with up to 3 fluorine atoms and up to 5 carbon atoms, or represents alkenyl or alkinyl with 3 to 5 carbon atoms, or represents cycloalkyl with 3 to 6 carbon atoms, or $R^3$ and $R^4$, together with the nitrogen atom, represent a 5-, 6- or 7-membered heterocyclic ring which can contain aza, oxa or thia elements and can optionally be substituted by alkyl groups.

Particularly preferred compounds of the formula (I) are those
in which
$R^1$ represents methyl, ethyl, n- or iso-propyl, 2,2-dimethylpropyl, 2-methoxyethyl, 2-ethoxyethyl, 2-methylthioethyl, 2-ethylthioethyl, 2,2,2-trifluoroethyl, cyanomethyl, cyanoethyl, allyl, methallyl, 2-propinyl, 1,1-dimethyl-2-propinyl, cyclopentyl or cyclohexyl, $R^2$ represents methyl, ethyl, n-propyl, iso-propyl, n-butyl, sec.-butyl, iso-butyl, tert.-butyl, phenyl or halogenophenyl, $R^3$ represents methyl, ethyl, n- or iso-propyl, 2,2-dimethylpropyl, 2-methoxyethyl, 2-ethoxyethyl, 2-propoxyethyl, 3-methoxypropyl, 3-ethoxypropyl, 3-butoxypropyl, 2-methylthioethyl, 2-ethylthioethyl, 2,2,2-trifluoroethyl, 2-cyanoethyl, 1-methyl-1-cyanoethyl, ω-cyanopentyl, allyl, methallyl, 2-propinyl, 1,1-dimethyl-2-propinyl, cyclopropyl, cyclobutyl, cyclopentyl, cyclohexyl, methoxy, ethoxy, n-propyloxy, n-butyloxy, sec.-butyloxy or n-pentyloxy, and $R^4$ represents hydrogen, methyl, ethyl, n- or iso-propyl, 2,2-dimethylpropyl, 2-methoxyethyl, 2-ethoxyethyl, 2-propoxyethyl, 3-methoxypropyl, 3-ethoxypropyl, 3-butoxypropyl, 2-methylthioethyl, 2-ethylthioethyl, 2,2,2-trifluoroethyl, 2-cyanoethyl, 1-methyl-1-cyanoethyl, ω-cyanopentyl, allyl, methallyl, 2-propinyl, 1,1-dimethyl-2-propinyl, cyclopropyl, cyclobutyl, cyclopentyl or cyclohexyl, or $R^3$ and $R^4$, together with the nitrogen atom, represent pyrrolidine, piperidine, 2-methylpiperidine, 3-methylpiperidine, 4-methylpiperidine, hexahydro-1H-azepine, morpholine, 2,6-dimethylmorpholine, thiazolidine, $N^1$-methylpiperazine or $N^1$-propylpiperazine.

Compounds of the formula (I) which may be mentioned in particular are those
in which
$R^1$ represents methyl, ethyl, isopropyl, n-propyl, sec.-butyl, cyclopentyl or cyclohexyl, $R^2$ represents methyl, ethyl, isopropyl, tert.-butyl or phenyl, $R^3$ represents methyl, butyl, or ω-cyanopentyl and $R^4$ represents hydrogen, or $R^3$ and $R^4$, together with the nitrogen atom, represent pyrrolidine, piperidine or morpholine.

If, for example, 2,5-bis-(cyclopentyloxycarbonyl)-3-methyl-4-hydroxythiophene and 2-methoxyethylamine are used as starting compounds for the preparation of the compounds of the formula (I) according to the invention, the course of the reaction can be represented by the following equation:

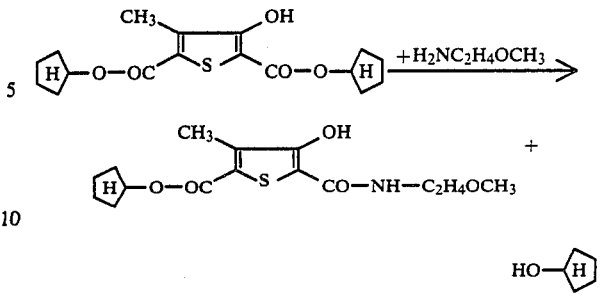

4-Hydroxythiophene derivatives, of which formula (II) provides a general definition, are required as starting substances for the reactions to give the compounds according to the invention. The starting compounds of the formula (II) are known to some cases, but can also be prepared by generally known processes, thus, for example, from thiodiacetic acid esters and 2-oxocarboxylic acid esters under alkaline conditions, for example under the action of potassium tert.-butylate, and after the condensation, the product is treated with an acid (compare European Pat. No. 93,384 and DAS (German Published Specification) No. 1,020,641). The reaction can be illustrated by the following equation:

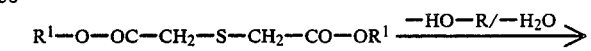

Compounds which may be mentioned specifically are: 3-methyl-4-hydroxy-thiophene-2,5-dicarboxylic acid methyl, ethyl, isopropyl, 1-methylpropyl, 2,2-dimethylpropyl, cyanomethyl, 2-cyanoethyl, 1-cyano-1-methylethyl, 2,2,2-trifluoroethyl, 2-methoxyethyl, 2-butylthioethyl, 2-ethylthioethyl, allyl, methallyl, propargyl, 1,1-dimethylpropargyl, cyclobutyl, cyclopentyl and cyclohexyl ester; and 4-hydroxy-3-ethyl-, -3-propyl-, -3-isopropyl-, -3-butyl-, -3-phenyl- and -3-tert.-butyl-thiophene-2,5-dicarboxylic acid 2,2,2-trifluoroethyl ester.

Primary and secondary amines of the formula (III), which are known from the literature, for example methylamine, dimethylamine, ethylamine, diethylamine, n-propylamine, di-n-propylamine, iso-propylamine, sec.-butylamine, iso-butylamine, n-butylamine, di-n-butylamine, amylamine, N-methylamylamine, 2-methoxyethylamine, 2-ethoxyethylamine, N-methyl-2-methoxyethylamine, 3-methoxypropylamine, 3-butoxypropylamine, 2-methylthioethylamine, 2-butylthioethylamine, N-methyl-3-butylthiopropylamine, 2-cyanoethylamine, 1-cyano-1-methylethylamine, ω-cyanopentylamine, 2,2-difluoroethylamine, 2,2,2-trifluoroethylamine, 3,3,3-trifluoropropylamine, 2,2-difluorobutylamine, 4,4,4-trifluorobutylamine, 1-trifluoromethylethylamine, allylamine, diallylamine, methallylamine, propargylamine, N-methylpropargylamine, cyclopropylamine, cyclobutylamine, cyclopentylamine, cyclohexylamine, N-methylcyclohexylamine, N-butoxyamine, N-methyl-N-butoxyamine, pyrrolidine, piperidine, 2-, 3- or 4-methylpiperidine, 2-ethylpiperidine, morpholine, 2,6-dimethylmorpholine, $N^1$-methylpiperazine, $N^1$-propylpiperazine, thiazolidine and hexahydro[1H]-azepine, are furthermore required for the reaction to give the compounds according to the invention.

Possible diluents for the process are all the organic solvents which are inert towards the reaction partners; polar solvents are preferably used. Examples which are to be mentioned here are: acetonitrile, dimethylacetamide, dimethylformamide, dimethylsulphoxide, N-methylpyrrolidone, dioxane, chlorobenzene, benzonitrile, ethyldiisopropylamine, triethylamine, tributylamine, dimethylcyclohexylamine, ethyldicyclohexylamine, dimethylbenzylamine, pyridine, picoline and quinoline, or the amine of the formula (III) to be reacted is used as the solvent.

The reaction temperatures and the reaction time are determined by the activity of the starting substances. In general, the reaction is carried out between about 20° and 180° C., preferably between 40° and 150° C.

In the case of reaction of low-boiling amines, it can be advantageous to carry out the reaction under pressure.

Depending on the operating conditions, the compounds according to the invention precipitate as crystals or remain dissolved in the organic solvent, and, after distilling off excess amine, which should be recovered as completely as possible, for economic reasons, and after washing with water and dilute acid, they can be isolated, during which they are deposited from their solutions, if appropriate, by addition of solvents of low polarity, such as cyclohexane, dibutyl ether or carbon tetrachloride.

The active compounds according to the invention exhibit a powerful fungicidal action and can be employed in practice for combating undesired fungi. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Some pathogens of fungal diseases which fall within the generic names listed above may be mentioned as examples but not by way of limitation: Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubense;* Plasmopara species, such as, for example, *Plasmopara viticola;* Peronospora species, such as, for example, *Peronospora pisi P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobulus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, *Fusarium culmorum;* Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae;* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, very fine capsules in polymeric substances and in coating compositions for seed, and ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl, ketone or cyclohexanone, strongly polar solvents, such as dimethylformamide and dimethyl sulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers their are suitable: for example ground natural minerals, such as kaolins, clays, talc, chalk, quartz, attapulgite, montmorillonite or diatomaceous earth, and ground synthetic minerals, such as highly dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthal-ocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom by further dilution, such as ready-to-use solutions, emulsifiable concentrates, emulsions, foams, suspensions, wettable powders, pastes, soluble powders, dusting agents and granules. They are used in the customary manner, for example by watering, spraying, atomizing, scattering, dusting, foaming, brushing and the like. It is furthermore possible to apply the active compounds by the ultra-low volume method or to inject the active compound formulation or the active compound itself into the soil. The seed of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

The compounds according to the invention can be used as intermediate products for the preparation of active secondary products.

PREPARATION EXAMPLES

Example 1

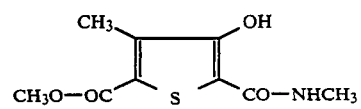

10 g of 2,5-bis-(methoxycarbonyl)-3-methyl-4-hydroxythiophene and 100 ml of benzonitrile are heated to 130° C. and a weak stream of methylamine is passed in for 15 hours.

The solvent is stripped off in vacuo. The residue is diluted with ethyl acetate and washed twice with 5% strength ice-cold sulphuric acid and twice with water. The mixture is dried over sodium sulphate and evaporated in vacuo and the evaporation residue is crystallized from 20 ml of methanol.

Yield: 1 g of 2-methoxycarbonyl-3-methyl-4-hydroxy-5-methylaminocarbonylthiophene Melting point: 190° C. (decomposition);

$H^1$-NMR; 80 MHz, $CDCl_3$+d-DMSO (δppm): 3H, s, 2.38 ($CH_3$); 3H, s, 3.88 ($CH_3OOC$—) and 3H, d 2.87 ($CH_3$—NH—).

EXAMPLE 2

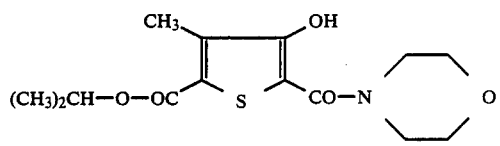

90 g of 2,5-bis-(isopropoxycarbonyl)-3-methyl-4-hydroxythiophene and 450 g of morpholine are heated at 124° C. for 9½ hours. The excess morpholine is evaporated off in vacuo. The evaporation residue is dissolved in 600 ml of methylene chloride and the solution is washed twice with ice-cold diluted sulphuric acid and once with water. It is dried with sodium sulphate. After evaporating off the solvent, the residue is triturated with a little diisopropyl ether, separated off and dried at 60° C./1 mbar. Yield: 78.9 g of 2-isopropoxycarbonyl-3-methyl-4-hydroxy-5-(1-aza-4-oxacyclohex-1-ylcarbonyl)-thiophene of melting point 123° C.

The compounds of the formula (I) are obtained in the same manner:

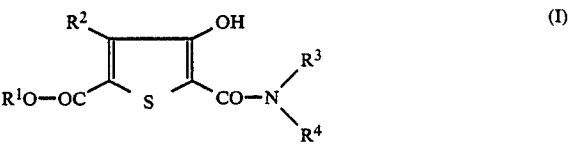

(I)

| Example | $R^1$ | $R^2$ | $R^3$ | $R^4$ | Melting point [°C.] |
|---|---|---|---|---|---|
| 3 | $H_5C_2$— | $H_3C$— | —$C_2H_4$—O—$C_2H_4$— | | 131 |
| 4 | n-$H_7C_3$— | " | " | | 126 |
| 5 | $C_2H_5(CH_3)CH$— | " | " | | 99 |
| 6 | $(CH_3)_2CH$— | " | —$C_5H_{10}$— | | 86 |
| 7 | " | " | —$C_4H_8$— | | 134 |
| 8 | " | " | —$(CH_2)_5CN$ | H | 94 |
| 9 | " | " | —$C_6H_{11}$ | H | 124 |
| 10 | $H_3C$— | $(CH_3)_2CH$— | —$C_2H_4$—O—$C_2H_4$— | | 115 |

-continued

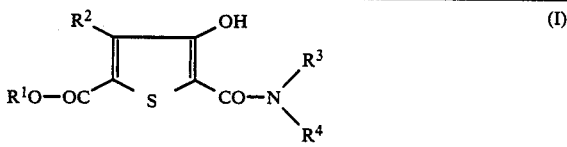

| Example | R¹ | R² | R³ | R⁴ | Melting point [°C.] |
|---|---|---|---|---|---|
| 11 | (cyclopentyl) | H₃C | " |  | 123 |
| 12 | C₂H₅(CH₃)CH— | H₃C |  | —C₅H₁₀— | viscous |
| 13 | " | " | —C₂H₄OCH₃ | H | 79 |
| 14 | H₃C— | " | " | " | 99 |
| 15 | H₅C₂— | " |  | —C₅H₁₀— | 89 |
| 16 | n-H₇C₃— | " |  | —C₅H₁₀— | 74 |

USE EXAMPLE

The compound shown below is employed as the comparison substance in the use example which follows:

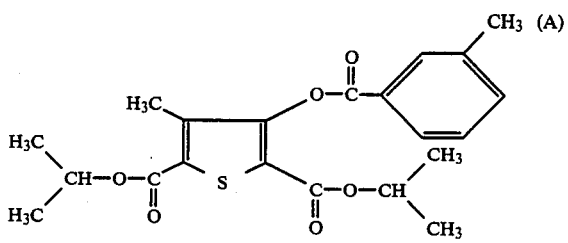

Example A

Pyricularia test (rice)/protective

Solvent: 12.5 parts by weight of acetone
Emulisifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried off, the plants are inoculated with an aqueous spore suspension of *Pyricularia oryzae*. The plants are then placed in a greenhouse at 100% relative atmospheric humidity and 25° C.

Thereafter, the plants remain in a greenhouse at a temperature of 25° C. and a relative atmospheric humidity of 100% until they are evaluated.

Evaluation of the disease infestation is carried out 4 days after the inoculation.

In this test, for example, a clearly superior activity compared with the prior art is shown by the compound according to preparation Example 1.

It will be understood that the specification and examples are illustrative but not limitative of the present invention and that other embodiments within the spirit and scope of the invention will suggest themselves to those skilled in the art.

We claim

1. An alkoxycarbonyl-substituted hydroxythiophene-carboxamide of the formula

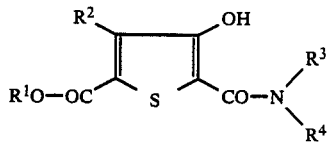

in which
  R¹ represents alkyl, alkoxyalkyl, alkylthioalkyl, fluoroalkyl, cyanoalkyl, alkenyl or alkinyl or represents cycloalkyl,
  R² represents alkyl or optionally substituted phenyl,
  R³ represents alkyl, alkoxyalkyl, alkylthioalkyl, cyanoalkyl, fluoroalkyl, alkenyl, alkinyl, cycloalkyl or alkoxy and
  R⁴ represents hydrogen, alkyl, alkoxyalkyl, alkylthioalkyl, fluoroalkyl, cyanoalkyl, alkenyl, alkinyl or cycloalkyl, or
  R³ and R⁴, together with the nitrogen atom, represent a heterocyclic radical which is optionally substituted by alkyl and can be further substituted in the alkylene chain by oxygen, sulphur or nitrogen.

2. An alkoxycarbonyl-substituted hydroxythiophene-carboxamide according to claim 1,
in which
  R¹ represents alkyl with 1 to 5 carbon atoms, or represents alkoxyalkyl or represents alkylthioalkyl with 1 to 5 carbon atoms per alkyl part, or represents fluoroalkyl with in each case up to 5 fluorine and carbon atoms, or represents cyanoalkyl with 1 to 5 carbon atoms in the alkyl part, or represents alkenyl with 3 or 4 carbon atoms, or represents alkinyl with 3 to 5 carbon atoms, or represents cycloalkyl with 4 to 6 carbon atoms,
  R² represents alkyl with 1 to 4 carbon atoms or optionally mono- to independently penta-substituted phenyl, substituents being alkyl with 1 to 4 carbon atoms, alkoxy or alkylthio with 1 to 4 carbon atoms in each case, halogen, nitro, halogenalkyl, halogenoalkoxy or halogenoalkylthio with 1 to 4 carbon atoms and 1 to 5 halogen atoms in each case
  R³ represents alkyl with 1 to 5 carbon atoms, or represents alkoxyalkyl or alkylthioalkyl with in each case 1 to 5 carbon atoms per alkoxy part, or represents cyanoalkyl with 1 to 5 carbon atoms in the alkyl part, or represents fluoroalkyl with up to 3 fluorine atoms and up to 5 carbon atoms, or represents alkenyl or alkinyl with 3 to 5 carbon atoms, or represents cycloalkyl with 3 to 6 carbon atoms, or represents alkoxy with 1 to 5 carbon atoms and $R^4$ represents hydrogen or alkyl with 1 to 5 carbon atoms, or represents alkoxyalkyl or alkylthioalkyl with in each case 1 to 5 carbons atoms per alkyl part, or represents cyanoalkyl with 1 to 5 carbon atoms in the alkyl part, or represents fluoroalkyl with up to 3 fluorine atoms and up to 5 carbon atoms, or represents alkenyl or alkinyl with 3 to 5 carbon atoms, or represents cycloalkyl with 3 to 6 carbon atoms, or $R^3$ and $R^4$, together with the nitrogen atom, represent a 5-, 6- or 7-membered heterocyclic ring which may contain at least one aza, oxa or thia element and is optionally substituted by at least one alkyl group.

3. An alkoxycarbonyl-substituted hydroxythiophene-carboxamide according to claim 1, in which $R^1$ represents methyl, ethyl, n- or iso-propyl, 2,2-dimethylpropyl, 2-methoxyethyl, 2-ethoxyethyl, 2-methylthioethyl, 2-ethylthioethyl, 2,2,2-trifluoroethyl, cyanomethyl, cyanoethyl, allyl, methallyl, 2-propinyl, 1,1-dimethyl-2-propinyl, cyclopentyl or cyclohexyl, $R^2$ represents methyl, ethyl, n-propyl, iso-propyl, n-butyl, sec.-butyl, iso-butyl, tert.-butyl, phenyl or halogenphenyl, $R^3$ represents methyl, ethyl, n- or iso-propyl, 2,2-dimethylpropyl, 2-methoxyethyl, 2-ethoxyethyl, 2-propoxyethyl, 3-methoxypropyl, 3-ethoxypropyl, 3-butoxypropyl, 2-methylthioethyl, 2-ethylthioethyl, 2,2,2-trifluoroethyl, 2-cyanoethyl, 1-methyl-1-cyanoethyl, ω-cyanopentyl, allyl, methallyl, 2-propinyl, 1,1-dimethyl-2-propinyl, cyclopropyl, cyclobutyl, cyclopentyl, cyclohexyl, methoxy, ethoxy, n-propyloxy, n-butyloxy, sec.-butyloxy or n-pentyloxy, and $R^4$ represents hydrogen, methyl, ethyl, n- or iso-propyl, 2,2-dimethylpropyl, 2-methoxyethyl, 2-ethoxyethyl, 2-propoxyethyl, 3-methoxypropyl, 3-ethoxypropyl, 3-butoxypropyl, 2-methylthioethyl, 2-ethylthioethyl, 2,2,2-trifluoroethyl, 2-cyanoethyl, 1-methyl-1-cyanoethyl, ω-cyanopentyl, allyl, methallyl, 2-propinyl, 1,1-dimethyl-2-propinyl, cyclopropyl, cyclobutyl, cyclopentyl or cyclohexyl, or $R^3$ and $R^4$, together with the nitrogen atom, represent pyrrolidine, piperidine, 2-methylpiperidine, 3-methylpiperidine, 4-methylpiperidine, hexahydro-1H-azepine, morpholine, 2,6-dimethylmorpholine, thiazolidine, $N^1$-methylpiperazine or $N^1$-propylpiperazine.

4. An alkoxycarbonyl-substituted hydroxythiophene-carboxamide according to claim 1, in which $R^1$ represents methyl, ethyl, isopropyl, n-propyl, sec.-butyl, cyclopentyl or cyclohexyl, $R^2$ represents methyl, ethyl, isopropyl, tert.-butyl or phenyl, $R^3$ represents methyl, butyl or ω-cyanopentyl and $R^4$ represents hydrogen, or $R^3$ and $R^4$, together with the nitrogen atom, represent pyrrolidine, piperidine or morpholine.

5. An alkoxycarbonyl-substituted hydroxythiophene-carboxamide according to claim 1, wherein such compound is 2-methoxycarbonyl-3-methyl-4-hydroxy-5-methylaminocarbonylthiophene of the formula

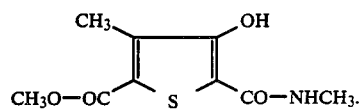

6. A fungicidal composition comprising a fungicidally effective amount of an alkoxycarbonyl-substituted hydroxythiophene-carboxamide according to claim 1 and a diluent.

7. A method of combating fungi which comprises applying to such fungi or to a fungus habitat a fungicidally effective amount of an alkoxycarbonyl-substituted hydroxythiophene-carboxamide according to claim 1.

8. A method of combating fungi which comprises applying to such fungi or to a fungus habitat a fungicidally effective amount of an alkoxycarbonyl-substituted hydroxythiophene-carboxamide according to claim 5.

* * * * *